United States Patent [19]

Knifton

[11] Patent Number: 4,661,609

[45] Date of Patent: Apr. 28, 1987

[54] PROCESS FOR COSYNTHESIS OF ETHYLENE GLYCOL AND DIMETHYL CARBONATE

[75] Inventor: John F. Knifton, Austin, Tex.

[73] Assignee: Texaco Inc., White Plains, N.Y.

[21] Appl. No.: 891,093

[22] Filed: Jul. 31, 1986

[51] Int. Cl.$^4$ .................... C07C 68/06; C07C 27/00
[52] U.S. Cl. .................................... 558/277; 568/858
[58] Field of Search .................... 568/858; 558/277

[56] References Cited

U.S. PATENT DOCUMENTS 3,803,201  4/1974  Gilpin et al. .................. 568/858 X
4,181,676  1/1980  Buysch et al. ................ 558/277 X
4,307,032 12/1981  Krimm et al. .................... 558/277

*Primary Examiner*—Bernard Helfin
*Attorney, Agent, or Firm*—Jack H. Park; Kenneth R. Priem; Cynthia L. Kendrick

[57] ABSTRACT

A process is disclosed for the cosynthesis of ethylene glycol and dimethyl carbonate by reacting methanol and ethylene carbonate in the presence of a catalyst selected from the group consisting of zirconium, titanium and tin.

12 Claims, No Drawings

PROCESS FOR COSYNTHESIS OF ETHYLENE GLYCOL AND DIMETHYL CARBONATE

This invention concerns a process for cosynthesis of ethylene glycol and dimethyl carbonate by the transesterification reaction of ethylene carbonate and methanol in the presence of homogeneous and heterogeneous catalysts from the group consisting of zirconium, titanium, tin oxides, salts and complexes. In addition to the fact that substantially fewer moles of methanol are needed in the methanol-ethylene carbonate feedstock per mole of dimethyl carbonate produced, this invention is advantageous in that the catalysts are in many cases found to perform better than sodium carbonate, which has been used in the art.

BACKGROUND OF THE INVENTION

Generally the prior art reports that the transesterification of aliphatic hydroxy compounds with carbonic acid, aliphatic diesters and aromatic diesters occurs readily in the presence of a basic catalyst and is a convenient method of synthesis of higher carbonates.

Several references deal with the transesterification of glycol carbonates using an aliphatic alcohol. Most demonstrate the use of methanol and ethylene carbonate.

U.S. Pat. No. 4,307,032 discloses a process for the preparation of a dialkyl carbonate by contacting a glycol carbonate of a 1,2-diol containing 2 to 4 carbon atoms with a selected alcohol to form the corresponding carbonate of said alcohol at a temperature of between 50 and 250° C, in the presence of an improved catalyst which is a thallium compound, allowing the reaction to take place under milder conditions. Thallium is however expensive and very toxic.

In another process disclosed in U.S. Pat. No. 4,181,676 there is taught a method for preparation of dialkyl carbonate by contacting a glycol carbonate of a 1,2-diol having 2 to 4 carbon atoms with a selected group of alcohols at an elevated temperature in the presence of an alkali metal or alkali metal compound wherein the improvement comprises employing less than 0.01 percent by weight of alkali metal or alkali metal compound based on the weight of the reaction mixture.

It is known that alkyl carbonates of the type ROCOOR can be obtained from alcohols and cyclic carbonates corresponding to the above formula through a transesterification reaction in the presence of alkali alcoholates or hydrates; however, moderate amounts of inorganic compounds are produced by these reactions and must be removed by methods which may unfavorably affect the general economy of the process.

In U.S. Pat. No. 4,062,884 this problem was addressed and it was found that dialkyl carbonates can be prepared by reacting alcohols with cyclic carbonates in the presence of organic bases, which makes it unnecessary to remove inorganic compounds and allows the catalyst to be totally recovered by means of simple distillation. The preferred organic base is a tertiary aliphatic amine.

U.S. Pat. No. 4,349,486 teaches a monocarbonate transesterification process comprising contacting a beta-fluoroaliphatic carbonate, a compound selected from the class of monohydroxy aliphatic alcohols, monohydroxy phenols and ortho-positioned dihydroxy aromatic compounds in the presence of a base. This invention claims to greatly reduce undesirable side reactions and only small amounts of carbonic acid-aliphaticaromatic mixed diester are associated with the isolated aromatic monocarbonate reaction.

The Gilpin and Emmons Patent, referred to above, discusses problems associated with the separation of the methanol, dimethyl carbonate azeotrope and teaches one solution, wherein dimethyl carbonate is isolated from the azeotrope by a combination of low temperature crystallization and fractional distillation.

In another article in the *J. Org. Chem.* 49(b) 1122–1125 (1984) Cella and Bacon discuss the results of their work. Among other things, they found that the alkylation of alkali metal bicarbonate and carbonate salts with alkyl halides in dipolar aprotic solvents and phase-transfer catalysts produces alkyl carbonates in good yields. The major limitation of this method is the failure of activated aryl halides or electronegatively substituted alkyl halides to produce carbonates due to the facility with which the intermediate alkoxy carbonate salts decompose.

Disadvantages of the methods discussed above include in many cases the fact that it is necessary to use a large amount of methanol feedstock relative to the amount of dimethyl carbonate produced. Also, in many cases, alkali metal halides are coproduced and these halides present disposal problems.

It would be a substantial advance in the art to devise an efficient process for co-producing dimethyl carbonate and ethylene glycol, which was homogenous and did not necessitate difficult product-catalyst separations. The dimethyl carbonate produced by this novel process can be used as a gasoline extender.

SUMMARY OF THE INVENTION

This invention concerns a process for the cosynthesis of ethylene glycol and dimethyl carbonate from ethylene carbonate and methanol by reacting ethylene carbonate and methanol in the presence of a homogeneous or heterogeneous catalyst selected from the group consisting of zirconium, titanium and tin oxides, salts or complexes thereof, at a temperature of from 20° C. to 200° C. and an operative pressure of zero to 5000 psig, until the desired products are formed.

A particular advantage of these systems over the prior art is the high selectivities to dimethyl carbonate (DMC) and ethylene glycol (EG)-basis the ethylene carbonate (EC) and methanol (MeOH) charged. These selectivities are illustrated in the accompanying Example I for the zirconium acetylacetonate catalyst and Example X for the zirconium diperchlorate oxide catalyst precursor.

DETAILED DESCRIPTION OF THE INVENTION

In the narrower and more preferred practice of this invention dimethyl carbonate and ethylene glycol are prepared simultaneously by a transesterification process which comprises reacting ethylene carbonate and methanol in the presence of a homogeneous zirconium, titanium or tin catalyst, at a temperature of between 50° C and 150° C, and a pressure of at least 50 psig, until the desired products are formed.

Starting materials employed in the process are an aliphatic alcohol and an aliphatic carbonate. Alcohols which work in the process of this invention include the monohydric alcohols containing one to 14 carbon atoms, including methanol, ethanol, isopropanol and isobutanol. Methanol is the preferred alcohol. Alkylene carbonates which will work in the process of this invention include the carbonate derivatives of 1,2-diols containing two to 10 carbon atoms per molecule, including ethylene carbonate, 1,2-propylene carbonate and 1,2-butanediol carbonate. Ethylene carbonate is the preferred alkylene carbonate feedstock for this process. The preferred starting materials are illustrated in the accompanying examples. Recovery of the desired ethylene glycol and dimethyl carbonate can generally be carried out by distillation and crystallization.

More specifically, methanol and ethylene carbonate are pumped into a tubular reactor upflow at a flow rate of 0.1 to 100 liquid hourly space velocity (LHSV). The reactor temperature is held at between 20° and 200° C. and a back pressure of zero to 5000 psi is maintained thorughout the experiment.

The homogeneous catalyst systems suitable for the practice of this invention generally comprise a zirconium, titanium or tin compound. The compound can be in the form of a salt or complex.

The zirconium-containing catalyst compound comprises a salt of zirconium or a complex. Suitable examples include zirconium salts of strong (mineral) acids, such as zirconium tetrachloride, $ZrCl_4$, zirconium bromide, $ZrBr_4$, zirconium fluoride, zirconium nitrate, zirconium sulfate, $Zr(SO_4)_2.4H_2O$, zirconium mixed halides and zirconium tetraiodide, zirconium alkoxides such as zirconium methoxide, zirconium ethoxide and zirconium isopropoxide, zirconium salts of weak acids such as zirconium acetate and zirconium acetylacetonate, $Zr(O_2C_5H_7)_4$, as well as zirconium compounds containing the zirconyl moiety, as for example, zirconium diperchlorate oxide, $ZrO(CLO_4)_2.8H_2O$ and zirconium oxide nitrate, $ZrO(NO_3)_2.X\ H_2O$.

The preferred zirconium catalyst precursors are zirconium acetylacetonate and zirconium diperchlorate oxide.

The titanium-containing catalyst compound may likewise comprise a salt of titanium or a complex. Suitable examples include titanium methoxide; other titanium alkoxides such as titanium isopropoxide, titanium acetate and titanium acetylacetonate also work. The preferred titanium compound is titanium isopropoxide.

Suitable tin-containing catalyst precursors for EC/MeOH transesterification include compounds such as tin(II) 2-ethylhexanoate, tin methoxide, dimethyltin salts, dibutyltin acetate and tributyltin chloride. The preferred tin compound is tin(II) 2-ethylhexanoate.

Also in some cases, the analogous zirconium, titanium and tin heterogeneous catalyst precursors may also be effective. Examples of suitable heterogeneous catalysts for the desired ethylene carbonate-methanol transesterification include zirconium oxide, $ZrO_2$, and titanium oxide. Said heterogeneous zirconium or titanium catalysts may be in the form of pellets, extrudates, granules or powders. Also effective may be zirconium carbide, zirconium nitride and zirconium silicate.

A particularly effective catalyst for the cosynthesis of dimethyl carbonate and ethylene glycol is a solution of zirconium diperchlorate oxide dissolved in the ethylene carbonate-methanol feed mix. This reaction solution is illustrated in accompanying Example X.

During the cosynthesis of ethylene glycol and dimethyl carbonate by the reaction of ethylene carbonate with methanol, a large excess of methanol is normally employed in the prior art. Usually the initial molar ratio of methanol to ethylene carbonate is in the range of 5 or greater, and preferably at least 10. This preferred ratio range is illustrated by U. S. Pat. No. 3,803,201 (1974). In the practice of this invention, by contrast, the initial weight ratio of ethylene carbonate to methanol is preferably 2 to 5. Such a range of weight ratios is illustrated by the accompanying examples.

Potential advantages to operating at this ethylene carbonate-to-methanol weight ratio include:
(a) More efficient transesterification.
(b) Lower levels of methanol required to be recycled after the transesterification step.

Ethylene glycol-dimethyl carbonate synthesis using the homogeneous catalyst described SUPRA can be conducted at reaction temperatures in the range from 20° to 200° C. The preferred operating temperature range is 50°-150° C.

The reaction can be conducted under atmospheric pressure. A pressure reactor is nevertheless required in the case of low-boiling point components if the reaction is to be carried out in the upper temperature range and in the liquid phase. The pressure is not critical. In general the reaction is allowed to proceed under the autogenous pressure of the reactants. However, the reaction can also be carried out under elevated pressure, for example, under an inert atmosphere. A pressure of zero to 5000 psig is appropriate here. An operating pressure of greater than 50 psig is suitable and the preferred pressure was in the range of 50 to 150 psi.

The residence time for the ethylene carbonate and methanol reactants in the tubular reactor may vary over a wide range according to the temperature of reaction, the molar ratios of carbonate/alcohol feedstocks, etc. Using the homogeneous catalysts of this invention, the necessary residence time in the reactor may range from 0.01 hours to 10 hours, although it may be extended beyond 10 hours without danger of additional by-products being formed. The preferred residence time is in the range of 0.1 to 5 hours.

The desired products of this process according to the invention are ethylene glycol and dimethyl carbonate. By-products include diethylene glycol, 1,1-dimethoxyethane, 1,2-dimethoxyethane, methyl 1,3-dioxolane, glycol monomethyl ether and dimethyl ether.

Products have been identified in this work by gas chromatography (gc), NMR, IR and gc-IR or a combination of these techniques. Zirconium and titanium analyses were by atomic absorption (AA). All liquid product analyses have, for the most part, been by gc; all temperatures are in degrees centigrade and all pressures in pounds per square inch gauge.

The following examples illustrate the novel process of this invention. The examples are only for illustrating the invention and are not considered to be limiting:

EXAMPLE I

This example illustrates the cosynthesis of dimethyl carbonate and ethylene glycol from ethylene carbonate plus methanol, in good selectivity, using a homogeneous zirconium catalyst derived from zirconium acetylacetonate dissolved in the EC/MeOH feed mix. The weight ratio of ethylene carbonate to methanol is 2:3.

To a 1 kg mixture of ethylene carbonate (EC) and methanol (typical composition: 59.0% MeOH, 41.0% EC) was added 50 g of zirconium acetylacetonate. The mixture was stirred to dissolve the zirconium salt, cooled in wet ice and the clear solution pumped through a 50 cc capacity, stainless steel, tubular reactor upflow at a rate of 25 cc/hr. The reactor temperature was held at 130° C and a back-pressure of 100 psi was maintained throughout the experiment. After feeding the ethylene carbonate-methanol mix for several (3–8) hours, the liquid effluent was sampled at regular time intervals and analyzed by gas-liquid chromatography.

Typically, this liquid effluent had the following composition:
10.8 wt % dimethyl carbonate (DMC)
6.9 wt % ethylene glycol (EG)
30.4 wt % ethylene carbonate (EC)
50.1 wt % methanol (MeOH).

Estimated molar selectivity to DMC, basic EC converted =

$$\frac{10.8/90}{(41.0 - 30.4)/88} \times 100 = >98\%$$

Estimated molar selectively to DMC, basic MeOH converted =

$$\frac{10.8/90 \times 2}{(59.0 - 50.1)/32} \times 100 = 86\%$$

EG selectivity basis EC converted:

$$\frac{6.9/62}{(41.0 - 30.4)/88} \times 100 = 92\%$$

EG selectivity basis MeOH converted:

$$\frac{6.9/62 \times 2}{(59.0 - 50.1)/32} \times 100 = 78\%$$

where DMC, FW=90.0; EC, FW=88.0; EG, FW=62.0; MeOH, FW=32.0.

EXAMPLES II to IX

Table 1 shows the cosynthesis of dimethyl carbonate and ethylene glycol from ethylene carbonate plus methanol using a variety of homogeneous zirconium, titanium and tin catalyst systems. Here the most effective catalyst precursors are:
zirconium acetylacetonate
tin(II) 2-ethylhexanoate
titanium isopropoxide.

EXAMPLE X

This example illustrates the cosynthesis of dimethyl carbonate and ethylene glycol from ethylene carbonate plus methanol, in good selectivity, using a homogeneous zirconium diperchlorate oxide catalyst precursor.

To a 1 kg mixture of ethylene carbonate and methanol (66.6% MeOH, 33.3 %EC) was added 50 g of zirconium diperchlorate oxide, $ZrO(ClO_4)_2 \cdot 8H_2O$. The mixture was stirred to dissolve the zirconyl salt (1.3% Zr), cooled in wet ice, and fed to the 50 cc tubular reactor at a rate of 25 cc/hr. using the procedures of Example I. The reactor temperature was held at 100° C, and a back pressure of 100 psi was maintained throughout the experiment.

Typical liquid effluent showed the following composition
10.4 wt % dimethyl carbonate
9.0 wt % ethylene glycol
24.2 wt % ethylene carbonate
54.2 wt % methanol.

The reactor temperature was then raised to 130° C. Typical liquid product now showed the following composition:
14.8 wt % dimethyl carbonate
9.0 wt % ethylene glycol
14.9 wt % ethylene carbonate
53.1 wt % methanol In the latter experiment:
Estimated molar selectivity to DMC, basis EC converted = 89%.
Estimated molar selectivity to DMC, basis MeOH converted = 76%.
Estimated molar selectivity to EG, basis EC converted = >98%.
Estimated molar selectivity to EG, basis MeOH converted = 95%.

EXAMPLE XI

This example also illustrates dimethyl carbonate/ethylene glycol cosynthesis, but uses a homogeneous zirconyl nitrate catalyst precursor.

To a 1 kg mixture of ethylene carbonate and methanol (57.0% MeOH, 38.5% EC) was added 50 g of zirconium dinitrate oxide, $ZrO(NO_3)_2 X H_2O$. The mixture

TABLE 1

| | DIMETHYL CARBONATE/ETHYLENE GLYCOL COSYNTHESIS[a] | | | | | | |
|---|---|---|---|---|---|---|---|
| | | Reactor Temp. | Feed Rate | Liquid Product (wt %) | | | |
| Example | Catalyst | (°C.) | cc/hr | DMC | EG | EC | MeOH |
| II | Zirconium tetrachloride | 130 | 25 | 5.6 | 3.6 | 41.2 | 46.0 |
| | " | 150 | 25 | 8.7 | 5.0 | 31.6 | 47.4 |
| III | Zirconium iso-propoxide[b] | 100 | 100 | 2.1 | 1.8 | 38.0 | 54.0 |
| IV | Zirconium acetyl-acetonate[b] | 110 | 100 | 5.5 | 4.0 | 36.9 | 51.8 |
| | | 150 | 25 | 11.4 | 7.6 | 31.8 | 47.0 |
| V | Titanium isopropoxide[b] | 100 | 100 | 4.7 | 1.8 | 30.4 | 52.9 |
| VI | Titanium acetylacetonate[b,d] | 110 | 25 | 0.1 | 0.1 | 52.5 | 46.1 |
| | " | 130 | 25 | 0.3 | 0.2 | 55.5 | 42.9 |
| | " | 150 | 25 | 1.0 | 0.6 | 49.4 | 47.8 |
| VII | Tin(II) 2-ethyl-hexanoate[c] | 100 | 100 | 5.8 | 2.2 | 35.1 | 55.8 |
| VIII | Dibutyltin acetate | 100 | 100 | 1.5 | 0.4 | 40.1 | 56.9 |
| IX | Tributyltin chloride | 100 | 100 | 0.2 | | 40.6 | 57.6 |

[a]Run in continuous, 50 cc capacity, tubular reactor, upflow at 25 cc/hr. liquid flow rate, 100 psi pressure, feed composition: 59% MeOH, 41% EC.
[b]Solution in EC/MeOH was filtered prior to use.
[c]Some catalyst precipitation during run.
[d]Feed composition: 52.5% MeOH, 47.5% EC.

was stirred to dissolve the zirconyl salt (1.5% Zr), cooled in wet ice, and fed to the 50 cc reactor at a rate of 25 cc/hr., as in Example I. The reactor temperature was held at 130° C, and a back pressure of 100 psi was maintained throughout the experiment.

Typical liquid effluent showed the following composition:
4.8 wt % dimethyl carbonate
8.3 wt % ethylene glycol
27.3 wt % ethylene carbonate
56.0 wt % methanol.

The reactor temperature was then raised to 150° C. Under these conditions the liquid product showed the following composition:
6.8 wt % carbonate
14.0 wt % ethylene glycol
24.1 wt % ethylene carbonate
52.5 wt % methanol.

EXAMPLE XII

This example illustrates the cosynthesis of dimethyl carbonate and ethylene glycol from ethylene carbonate plus methanol, in good selectivity, using a hetergeneous zirconium oxide catalyst.

To the 50 cc tubular reactor of Example I, packed with 3.2 mm pellets of zirconium oxide (98% $ZrO_2$), is pumped a solution of ethylene carbonate plus methanol (67.6% MeOH, 31.9% EC) at a rate of 50 cc/hr. Reactor temperature was held at 130° C, the back pressure was 100 psi. Typical liquid effluent showed the following composition.
3.8 wt % dimethyl carbonate
2.7 wt % ethylene glycol
29.9 wt % ethylene carbonate
63 1 wt % methanol.

The reactor temperature was then raised to 160° C. Typical liquid product under equillibrium conditions, using this higher reactor temperature were as follows:
7.9 wt % dimethyl carbonate
5.2 wt % ethylene glycol
25.2 wt % ethylene carbonate
60.8 wt % methanol.

No zirconium could be detected in the product liquid, basis atomic absorption analyses (AA).

What is claimed is:

1. A process for cosynthesis of ethylene glycol and dimethyl carbonate which comprises reacting ethylene carbonate and methanol in the presence of a homogeneous catalyst selected from the group consisting of soluble salts of zirconium, titanium and tin or complexes thereof, at a temperature of 20° to 200° C until the desired products are formed.

2. The process of claim 1 wherein the homogeneous catalyst is a salt or complex of zirconium from the group consisting of zirconium salts of strong (mineral) acids, zirconium alkoxides, zirconium salts of weak acids and zirconyl compounds.

3. The process of claim 2 wherein the homogeneous catalyst is a zirconium compound selected from the group consisting of zirconium acetylacetonate, zirconium diperchlorate oxide, zirconium methoxide, zirconium dinitrate oxide, zirconium tetrachloride and zirconium isopropoxide.

4. The process of claim 1 wherein the homogeneous catalyst is a salt or complex of titanium from the group consisting of titanium acetylacetonate, titanium isopropoxide and titanium methoxide.

5. The process of claim 1 wherein the homogeneous catalyst is a salt or complex of tin from the group consisting of tin 2-ethylhexanoate, tin methoxide, dibutyltin acetate and tributyltin chloride.

6. The process of claim 1 wherein the operating temperature is between 50° and 150° C.

7. The process of claim 1 wherein the operating pressure is between zero and 5000 psig.

8. The process of claim 1 wherein the weight ratio of methanol to ethylene carbonate is in the range of 2:1 to 5:1.

9. The process of claim 1 for cosynthesis of dimethyl carbonate and ethylene glycol which comprises feeding methanol and ethylene carbonate to a tubular reactor while maintaining a weight ratio of methanol to ethylene carbonate of between 2:1 to 5:1, in the presence of a soluble zirconium, titanium or tin salt or complex, while maintaining the reactor at a temperature of between 50° and 150° C and a pressure of at least 50 psig.

10. A process for cosynthesis of ethylene glycol and dimethyl carbonate by reacting ethylene carbonate and methanol containing a homogeneous catalyst dissolved therein from the group consisting of zirconium acetylacetonate, zirconium diperchlorate oxide, titanium isopropoxide and tin(II) ethylhexanoate.

11. The process of claim 1 wherein the cosynthesis of ethylene glycol and dimethyl carbonate from ethylene carbonate plus methanol is conducted in the presence of a heterogeneous catalyst selected from the group consisting of the oxides of zirconium and titanium.

12. The process of claim 11 wherein the heterogeneous catalyst is zirconium oxide.

* * * * *